United States Patent
Hamel (10) Patent No.: US 7,615,051 B2
(45) Date of Patent: Nov. 10, 2009

(54) CRANIOFACIAL FRACTURE REDUCTION ASSEMBLY

(75) Inventor: Ross Jonathan Hamel, West Chester, PA (US)

(73) Assignee: Synthes USA, LLC, West Chester, PA (US)

(*) Notice: Subject to any disclaimer, the term of this patent is extended or adjusted under 35 U.S.C. 154(b) by 0 days.

(21) Appl. No.: 10/783,233

(22) Filed: Feb. 19, 2004

(65) Prior Publication Data

US 2004/0167530 A1    Aug. 26, 2004

Related U.S. Application Data

(60) Provisional application No. 60/449,021, filed on Feb. 21, 2003.

(51) Int. Cl.
*A61B 17/62* (2006.01)

(52) U.S. Cl. .................. 606/56; 606/86 R; 606/105

(58) Field of Classification Search .............. 606/54, 606/56, 57, 58, 59, 61, 73, 90, 104, 105
See application file for complete search history.

(56) References Cited

U.S. PATENT DOCUMENTS

| | | | | |
|---|---|---|---|---|
| 2,055,024 A | * | 9/1936 | Bittner, Jr. ................... | 606/56 |
| 2,079,567 A | * | 5/1937 | Anderson ..................... | 602/39 |
| 2,273,954 A | | 2/1942 | Grass | |
| 2,477,562 A | * | 8/1949 | Anderson ..................... | 602/39 |
| 3,072,118 A | | 1/1963 | Standerwick et al. | |
| 3,196,875 A | * | 7/1965 | Pfeiffer ....................... | 606/129 |
| 3,892,232 A | | 7/1975 | Neufeld | |
| 3,941,123 A | | 3/1976 | Volkov et al. | |
| 3,961,854 A | * | 6/1976 | Jaquet ......................... | 403/59 |
| 4,127,119 A | | 11/1978 | Kronner | |
| 4,361,144 A | * | 11/1982 | Slatis et al. ................... | 606/54 |
| 4,365,624 A | * | 12/1982 | Jaquet ......................... | 606/56 |
| 4,602,622 A | * | 7/1986 | Bar et al. ..................... | 606/130 |
| 4,612,921 A | * | 9/1986 | Lazo de Zbikowski ........ | 606/72 |
| 4,628,144 A | * | 12/1986 | Burger ........................ | 136/256 |
| 4,628,922 A | * | 12/1986 | Dewar ......................... | 606/56 |
| 4,768,524 A | * | 9/1988 | Hardy ......................... | 606/54 |
| 4,821,716 A | | 4/1989 | Ghajar et al. | |
| 4,867,144 A | * | 9/1989 | Karas et al. .................. | 606/280 |
| 4,955,891 A | * | 9/1990 | Carol .......................... | 606/130 |
| 4,978,347 A | | 12/1990 | Ilizarov | |
| 4,978,350 A | * | 12/1990 | Wagenknecht ............... | 606/72 |
| 5,049,150 A | | 9/1991 | Cozad | |
| 5,067,954 A | | 11/1991 | Ilizarov | |
| 5,087,258 A | * | 2/1992 | Schewior ..................... | 606/56 |

(Continued)

*Primary Examiner*—Eduardo C Robert
*Assistant Examiner*—David Comstock
(74) *Attorney, Agent, or Firm*—Woodcock Washburn LLP (57) ABSTRACT

A Craniofacial Fracture Reduction Assembly may include a reduction platform, a threaded fragment manipulator, and an adjustable support assembly. The reduction platform has at least one receiving hole configured to accept a fragment manipulator. The fragment manipulator may comprise an elongated member having a bone engaging portion for engaging a targeted fractured bone piece and a center threaded portion. In use, the bone engaging end of the fragment manipulator is inserted through the receiving hole in the reduction platform and then into the fracture region where it engages the targeted fractured bone piece. Thereafter a reduction nut is threaded onto the non-engaged end of the fragment manipulator until the nose of the nut contacts the reduction platform. Continued rotation of the nut causes the fragment manipulator to be drawn up through the reduction nut, pulling the bone fragment toward the reduction platform, thereby reducing the fracture.

16 Claims, 11 Drawing Sheets

U.S. PATENT DOCUMENTS

| | | | |
|---|---|---|---|
| 5,129,899 A * | 7/1992 | Small et al. | 606/61 |
| 5,443,464 A * | 8/1995 | Russell et al. | 606/54 |
| 5,520,690 A * | 5/1996 | Errico et al. | 606/61 |
| 5,545,163 A * | 8/1996 | Miller et al. | 606/61 |
| 5,575,794 A | 11/1996 | Walus et al. | |
| 5,797,908 A | 8/1998 | Meyers et al. | |
| 5,938,663 A * | 8/1999 | Petreto | 606/61 |
| 6,244,795 B1 | 6/2001 | Fenelon | |
| 6,432,109 B1 * | 8/2002 | Letendart et al. | 606/61 |
| 6,530,925 B2 * | 3/2003 | Boudard et al. | 606/54 |
| 6,663,630 B2 * | 12/2003 | Farley et al. | 606/54 |
| 6,699,251 B1 * | 3/2004 | Venturini | 606/73 |
| 2001/0016744 A1 | 8/2001 | Kupferschmid et al. | |

\* cited by examiner

CRANIOFACIAL FRACTURE REDUCTION ASSEMBLY

CROSS REFERENCE TO RELATED APPLICATION

This claims the benefit of U.S. Provisional Application No. 60/449,021, filed Feb. 21, 2003.

BACKGROUND OF THE INVENTION

The present invention relates to an apparatus for the correction of craniofacial abnormalities, and more particularly to a minimally invasive device for reducing various fractures of the craniofacial skeleton.

When a major cranial injury is suffered (e.g., from a blow to the head), the craniofacial bones may be fractured and become depressed into the head cavity resulting in cranial abnormalities. Each individual bone piece must then be reduced in order to minimize the fracture and realign the craniofacial bones. During this procedure, the surgeon must precisely locate, engage and reduce the fractured bone pieces to ensure the patient's bone structure heals without long term abnormality.

Initial practices, which are still widely used today, require the fractured bones to be exposed by making a bi-coronal incision, and peeling the skin away from the affected area to allow access to the fracture site. Exposing the fractured skeleton allows the surgeon to identify, and with the use of traditional surgical instruments, realign, the fractured bone pieces. Surgical instruments, such as surgical elevators and spatulas, which are widely known in the art, permit surgeons to dig beneath the fractured bone to pry the bone pieces back into alignment. These devices, however, do not provide surgeons with precise control over the amount or direction of reduction. Furthermore, such invasive techniques increase a patient's chances for infection and facial scarring.

Another known surgical device used in such procedures is the "Carroll-Girard Screw," which is basically a self-tapping screw with a T-handle. The Carroll-Girard Screw improves upon surgical elevators and spatulas because it may not require a bi-coronal incision for access to the fracture site. Rather the surgeon may engage the fractured bone pieces using the Carroll-Girard Screw by simply making one or more incisions near the fracture. The Carroll-Girard Screw, however, requires a surgeon to pre-drill a pilot hole into the fractured bone pieces for proper engagement. Furthermore, similar to surgical elevators and spatulas, the Carroll-Girard Screw does not provide a surgeon with precise control over the amount or direction of reduction. Instead, the Carroll-Girard Screw depends exclusively upon the surgeon's manual dexterity to reduce and realign the fractured bone pieces.

Thus, there remains a need for a minimally invasive fracture reduction system that provides a surgeon with control over the amount of reduction to minimize cranial fractures and to realign the fractured bones as close as possible to their original shape. The present invention addresses this problem and others by providing a Craniofacial Fracture Reduction Assembly that utilizes a self-drilling threaded fragment manipulator, an alignment plate and preferably a reduction nut. The present invention is minimally invasive, requiring only a few minor incisions to accommodate the threaded fragment manipulator, and an optional viewing endoscope. This arrangement reduces the possibility of infection, scarring and decreases healing time. Finally, the present invention allows the surgeon to place the reduction system in a variety of locations above a patient's face, providing ideal access to the fracture location.

SUMMARY OF THE INVENTION

The present invention relates to a Craniofacial Fracture Reduction Assembly that provides reduction control for the reducing of fractured bone pieces. The Craniofacial Fracture Reduction Assembly preferably includes a reduction platform, a threaded fragment manipulator and optionally, supporting structure. The threaded fragment manipulator preferably works in combination with a variable angle reduction nut, resulting in accurate control over the reduction vector. The supporting structure preferably permits free mobility of the reduction platform to allow the surgeon to precisely position the reduction platform over the fracture region. The Craniofacial Fracture Reduction Assembly may also be used in combination with an endoscope (i.e., a fiber optic camera), which may be inserted under the patient's skin, further assisting the surgeon to locate the fractured bone pieces and to visualize the engagement of the threaded fragment manipulator with the targeted bone piece.

The present invention further relates to a fracture reduction assembly comprising a reduction platform, a threaded fragment manipulator and a reduction nut. The reduction platform may have a top surface, a bottom surface, and at least one receiving hole in communication with the top and bottom surfaces. Alternatively, for example, the reduction platform may be a cylindrical bar. The fragment manipulator may have a bone engaging end, and a threaded portion, the manipulator having a portion which is sized to fit within the receiving holes. The nut may be configured to threadably engage the fragment manipulator threaded portion and to engage the platform top surface.

The present invention further relates to a fracture reduction assembly for manipulating bone pieces comprising a reduction platform having a top surface, a bottom surface, and at least one receiving hole in communication with the top and bottom surfaces; and a fragment manipulator having a bone engaging end. The manipulator may have a portion which is sized to fit within the receiving holes, wherein at least a portion of the fragment manipulator has a threaded section configured to translate the fragment manipulator through the receiving hole to reduce the patient's bone. The fracture reduction assembly may further have a nut with a threaded portion configured to threadably engage the threaded section and an exterior surface configured to engage the top surface of the platform. Alternatively, the fracture reduction assembly may comprise receiving holes with threaded portions configured to threadably engage the threaded section of the fragment manipulator.

The present invention may further encompass a supporting structure. The supporting structure may be a standard external frame, or a standard head fixation assembly. Alternatively, the supporting system may be a customized external frame.

The present invention further relates to a method of performing a craniofacial reduction comprising the steps of locating at least a portion of a bone to be reduced; positioning a reduction platform over the located bone portion; inserting a fragment manipulator through the reduction platform and into the located bone portion; threading a nut onto the fragment manipulator until the nut contacts the reduction platform; and continuing to rotate the nut so that the fragment manipulator is drawn up through the nut thereby moving the located bone portion attached to the fragment manipulator.

DESCRIPTION OF THE PREFERRED EMBODIMENTS

Although the present device is described herein as a Craniofacial Fracture Reduction Assembly and shown as being utilized to reduce fractures in the cranial region, it should be understood that the current invention may be used to correct any cranial abnormality even if no actual fracture exists so long as bone reduction is required. Furthermore, it should be understood that the present invention may be adapted for reduction of bones in other areas of the body.

Figure 4:
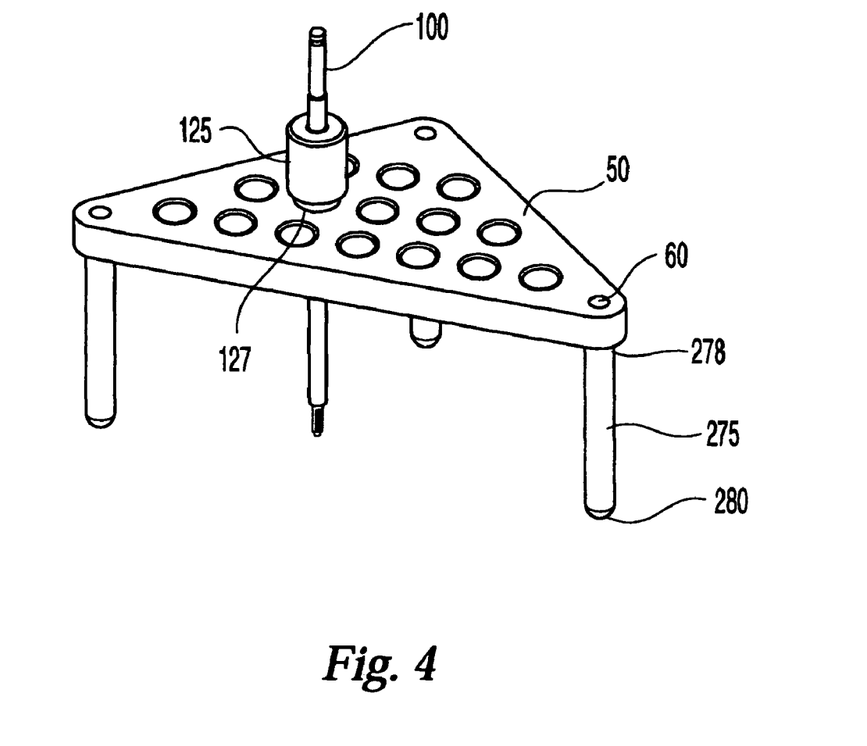
FIG. 4 is a perspective view of the reduction platform of FIG. 1 attached to supporting legs.

For the purpose of promoting an understanding of the principles of the present invention, reference will now be made to the embodiment illustrated in FIG. 1. As shown, the Craniofacial Fracture Reduction Assembly 10 generally includes a reduction platform 50, a threaded fragment manipulator 100 and optionally a supporting structure 150. Preferably, the supporting structure 150 allows multiple degrees of adjustment of the reduction platform 50 to permit precise positioning over the fractured region. Once the reduction platform 50 is properly positioned, the threaded fragment manipulator 100 is inserted through a receiving hole 70 (as shown in FIG. 2) in the reduction platform 50, and then inserted under the patient's skin where it engages the targeted fractured bone piece. A reduction nut 125 is then threaded onto the non-engaged end of the threaded fragment manipulator 100 until the nose 127 (as shown in FIG. 4) of the reduction nut 125 contacts the reduction platform 50. Once contact with the reduction platform 50 is made, continued rotation of the reduction nut 125 draws the threaded fragment manipulator 100 through the reduction nut 125, pulling the fractured bone piece upward toward the reduction platform 50. This process may be enhanced with the aid of an endoscope 300 (i.e., a fiber optic camera), which may be inserted through the skin in the scalp region. The surgeon may use the endoscope 300 to locate the fractured bone pieces, to visualize the engagement of the threaded fragment manipulator 100 with the bone pieces, and to observe the reduction.

Figure 2A:
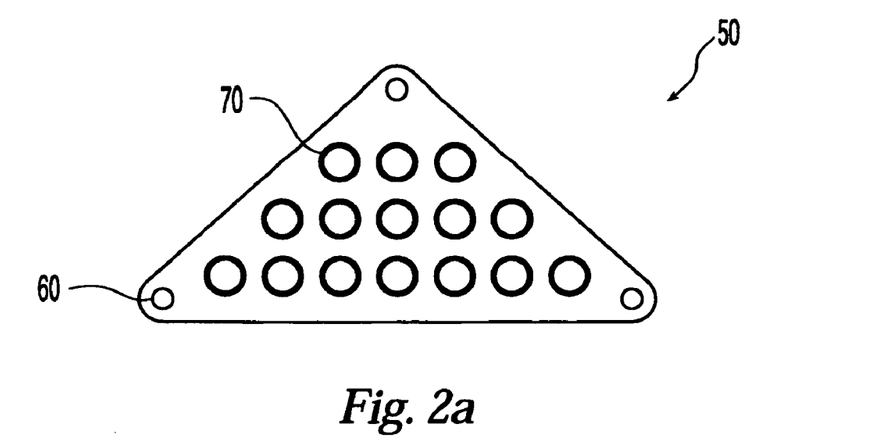
FIGS. 2A and 2B are a top view and a sectional view, respectively, of the reduction platform of FIG. 1.
Figure 2B:
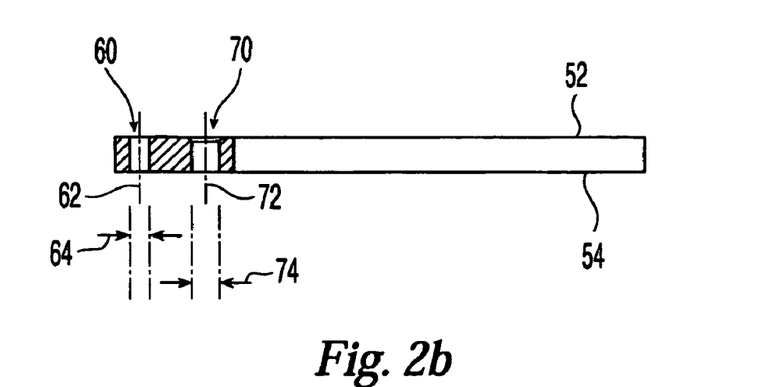
Figure 8:
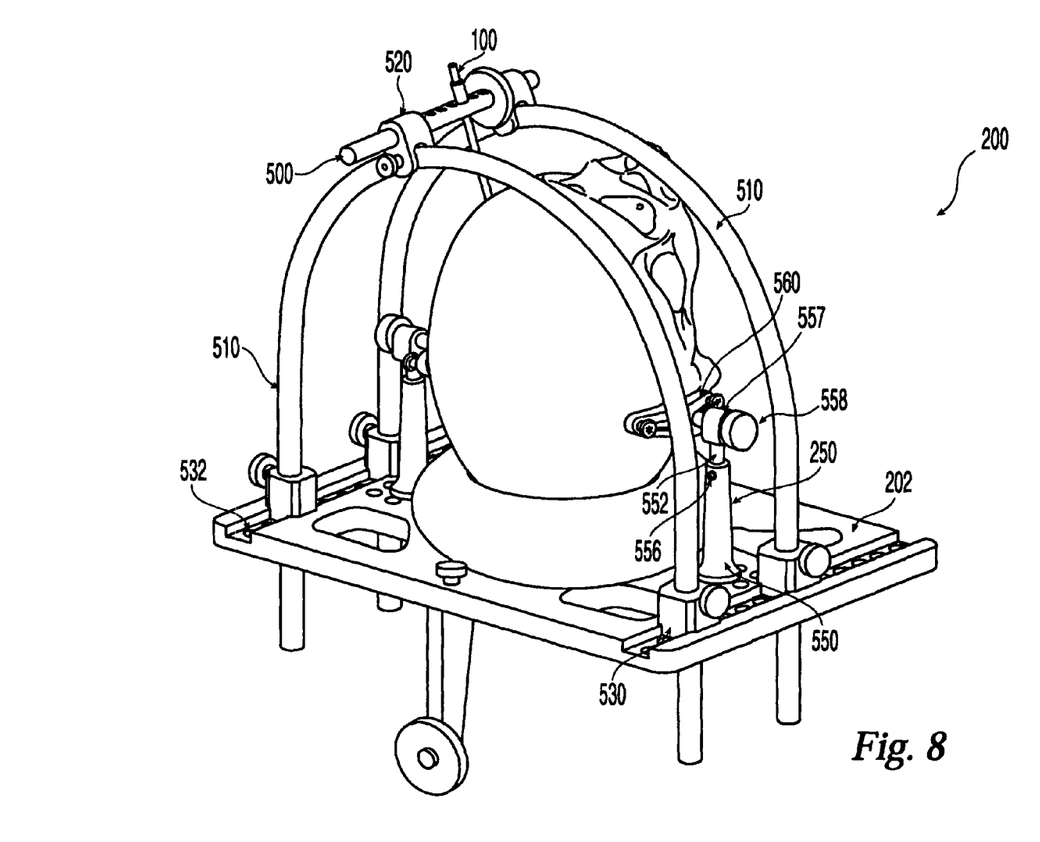
FIG. 8 is a perspective view of a further alternate embodiment of the reduction platform and external frame.
Figure 9:
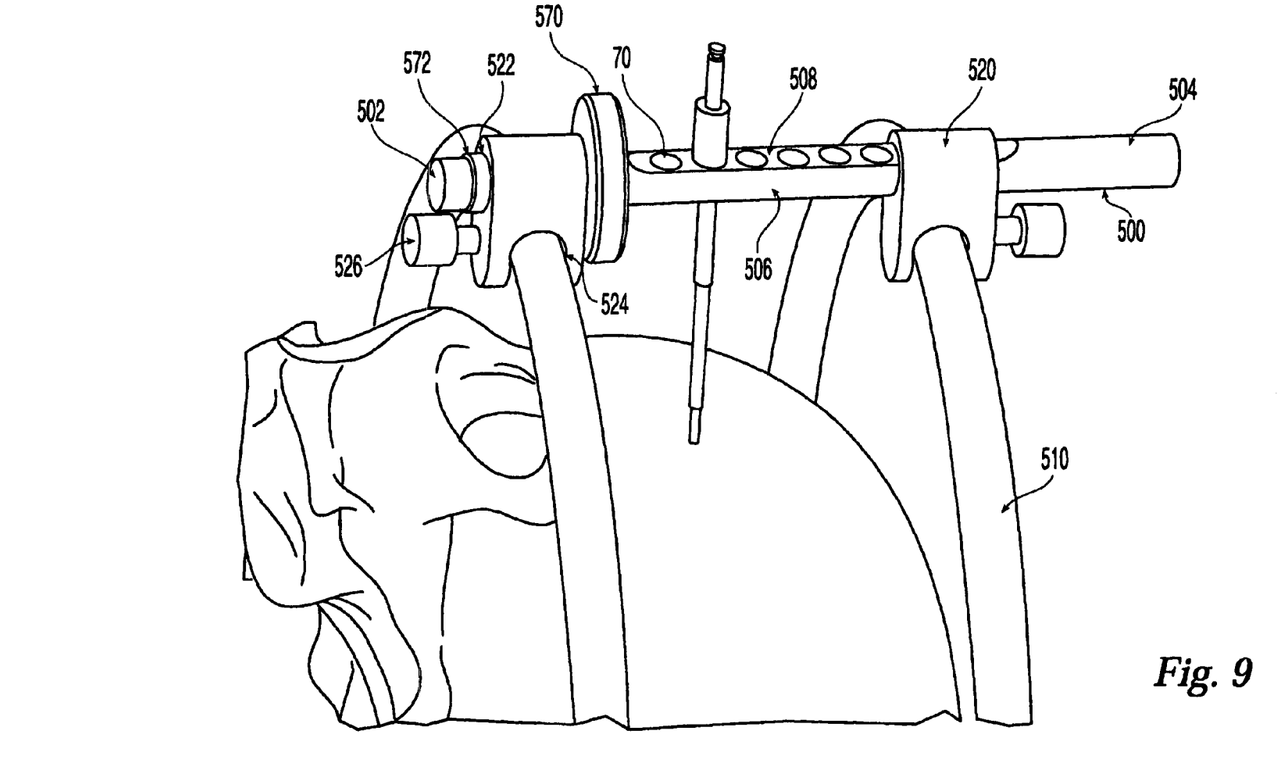
FIG. 9 is a detailed view of the reduction platform depicted in FIG. 8.

As illustrated in FIGS. 2A and 2B, the reduction platform 50 comprises top 52 and bottom 54 surfaces, the top surface 52 generally facing the surgeon during operation and the bottom surface 54 generally facing the patient. The top 52 and bottom 54 surfaces may take any shape, configuration or contour, preferably the surfaces are parallel. As depicted, the reduction platform 50, when viewed from the top, may have a triangular shape with rounded corners and edges. The reduction platform 50, however may take on any shape, including but not limited to rectangular, square, circular, oblong, ellipsoidal, trapezoidal, etc. Alternatively, as illustrated in FIGS. 8 and 9, the reduction platform 50 may be a cylindrical bar 500 with a first end 502, a second end 504 and a center portion 506 extending therebetween. As shown, a portion of the bar 500 may have a flat surface 508 for facilitating engagement with the threaded fragment manipulator 100, the flat surface 508 generally corresponding with the location of the receiving holes 70 (to be described in more detail below). Moreover, the cylindrical bar 500 may have a portion (not shown) which is externally threaded for engagement with internal threads on a thumb wheel 570 (to be described in more detail below).

The reduction platform 50 may further comprise at least one receiving hole 70 sized and configured to receive the threaded fragment manipulator 100, preferably the receiving holes are non-threaded to permit slidable engagement with the threaded fragment manipulator 100. The reduction platform 50 may however, contain any number of receiving holes 70 configured in any number of arrangements depending on the size and shape of the reduction platform 50 utilized. Preferably, the reduction platform 50 has multiple receiving holes 70, thus providing a surgeon with additional flexibility in positioning the threaded fragment manipulator 100 to engage bone pieces. Providing multiple receiving holes 70 further permits a surgeon to utilize multiple threaded fragment manipulators 100 at once, if necessary.

Figure 3A:
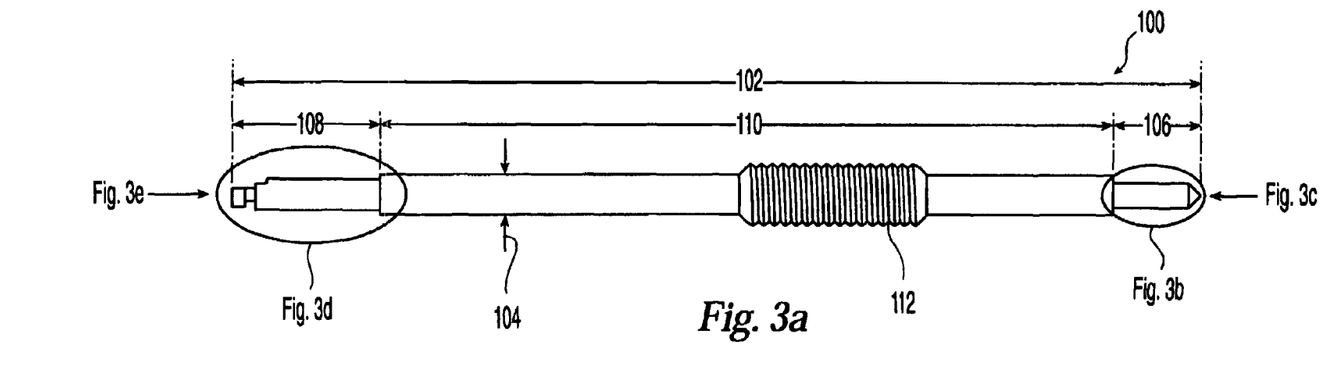
FIGS. 3A through 3F are detailed views of the threaded fragment manipulator.

As shown in FIG. 2B, the receiving holes 70 extend from the reduction platform top surface 52 to its bottom surface 54 and each has an axis 72 that is generally perpendicular to the plane of the top surface 52. It is noted that the receiving holes 70, however, may have an axis 72 that is angled relative to the top surface 52; the degree of such an angle being a matter of design choice. The receiving holes 70 may further have a diameter 74 which is generally larger than the central cross section 104 of the threaded fragment manipulator (as shown in FIG. 3A). The oversized nature of the receiving holes 70 permits the surgeon to insert the threaded fragment manipulator 100 at an angle relative to the axis 72 of the receiving holes, providing angular mobility for positioning the threaded fragment manipulator 100 during bone engagement and reduction.

At their intersection with the top surface 52, the receiving holes 70 may be countersunk, preferably semi-spherically countersunk, to provide a smooth surface for contacting the semi-spherical nose of the reduction nut 127 (see FIG. 4), which is described in more detail later.

Figure 2C:
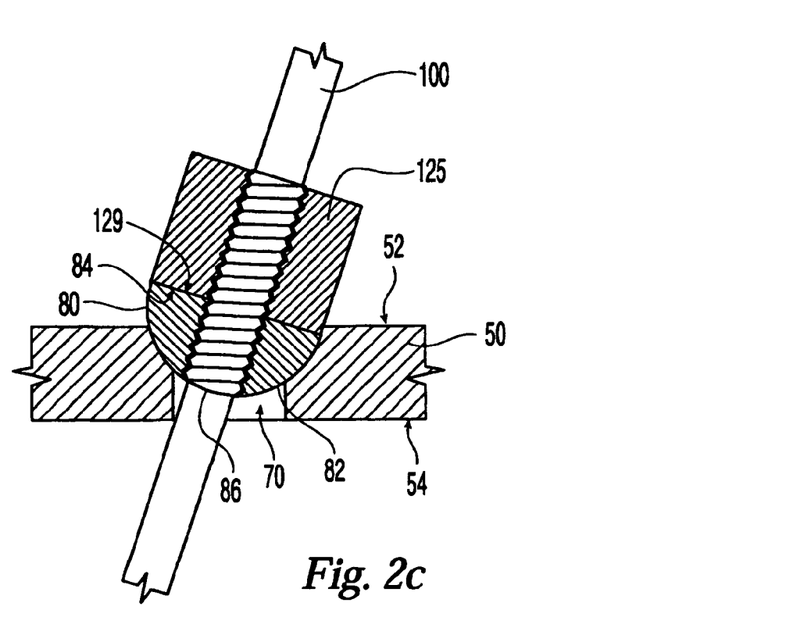
FIGS. 2C and 2D are perspective views of an optional insert for use with the reduction platform of FIG. 1.
Figure 2D:
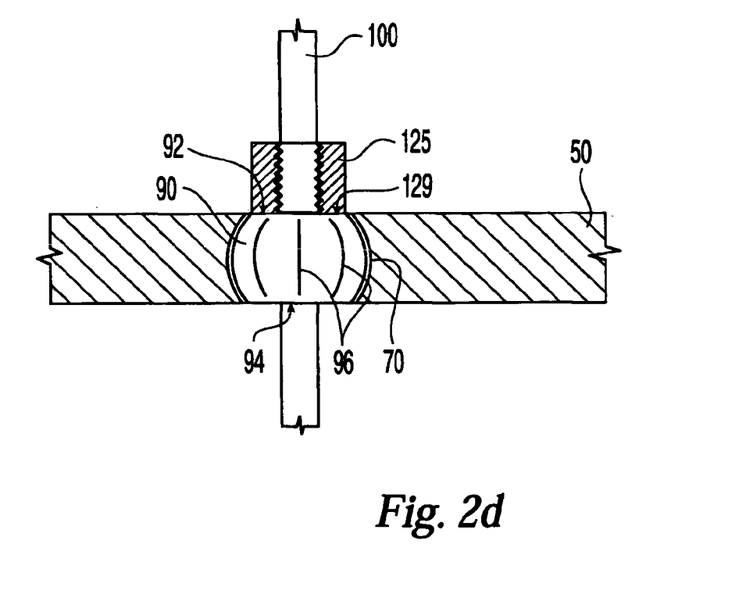

In an alternate embodiment, as shown in FIGS. 2C and 2D, an insert 80, 90 may be provided within at least a portion of one or more of the receiving holes 70, the insert 80, 90 having an axial bore 86, 94 configured to receive the threaded fragment manipulator 100. The insert 80, 90 may be freely slidable within at least a portion of the receiving hole 70, thus providing additional angular mobility in positioning the threaded fragment manipulator 100 during bone engagement and reduction. For example, the insert may be an articulating washer 80 (see FIG. 2C) which has a substantially spherical outer surface portion 82 configured to slidably engage the receiving hole 70 in the reduction platform 50. The articulating washer 80 may have a nut engaging portion 84 adjacent the spherical portion 82, the nut engaging portion 84 configured to provide a bearing surface for the flat nose 129 of the reduction nut 125. The articulating washer 80 may further have a bore 86 sized to receive the center portion 110 of the threaded fragment manipulator 100. The bore 86 may be smooth to slideably receive the threaded fragment manipulator 100, or the bore 86 may be threaded to engage the corresponding external threads 112 of the threaded fragment manipulator 100.

Alternatively, the insert may comprise a collar 90 (as shown in FIG. 2D) having a spherical outer surface configured and sized to slide within a correspondingly spherical inner surface of a reduction platform receiving hole 70. The collar 90 may have a top surface 92 configured to provide a bearing surface for the flat nose 129 of the reduction nut 125. The collar 90 may further have a bore 94 sized to receive the center portion 110 of the threaded fragment manipulator 100. The collar 90 may further comprise at least one vertical slot 96 which renders the collar 90 resiliently deformable, thus allowing the collar 90 to be snapped into, and retained within, the suitably sized spherical inner surface of a receiving hole 70. The bore 94 may be smooth to slideably receive the threaded fragment manipulator 100, or the bore 94 may be threaded to engage the corresponding external threads 112 of the threaded fragment manipulator 100.

Figure 1:
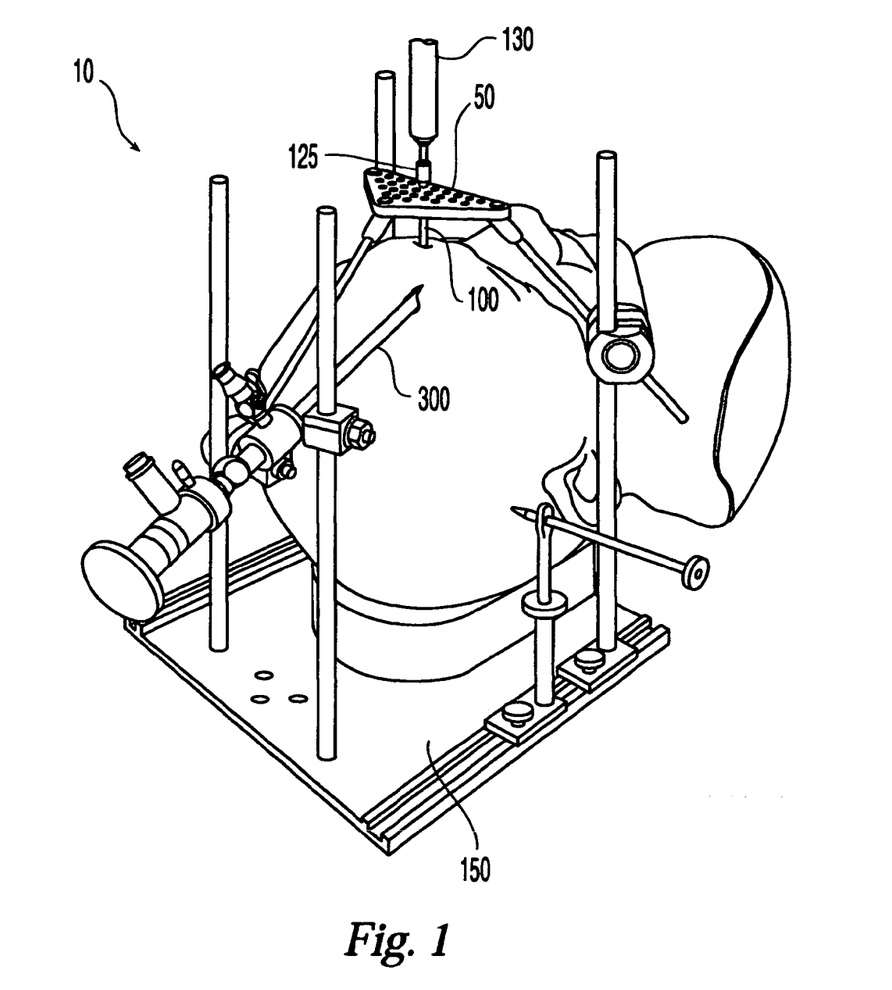
FIG. 1 is a perspective view of the Craniofacial Fracture Reduction Assembly according to one embodiment of the present invention.

Referring to FIG. 2A and 2B again, the reduction platform 50 may optionally include at least one fixation element 60 to allow connection to an optional supporting structure 150 (as shown in FIG. 1). The at least one fixation element 60 may be a bore which extends from the top surface 52 to the bottom surface 54 and generally has an axis 62 that is perpendicular to the plane of the top surface 52. The fixation element axis 62 may alternatively be angled relative to the top surface 52. As depicted in FIG. 2A, the reduction platform 50 has three fixation elements 60, one in each corner of the illustrated triangular plate. The fixation elements 60 each have a diameter 64 to permit attachment to the supporting structure 150. The number and arrangement of fixation elements 60 may vary according to the size and shape of the reduction platform 50 used, and the arrangement of the corresponding support structure 150, if used.

The reduction platform 50 may be manufactured from a variety of materials, including but not limited to stainless steel, aluminum, titanium, titanium alloy, carbon fiber, plastic or any other suitable material known in the art.

As shown in FIG. 3A, the threaded fragment manipulator 100 comprises an elongated member, for example, a shaft, rod, etc. having a length 102, a central cross section 104, a bone engaging end 106, a center adjustment portion 110 and optionally a tool engaging end 108, at least a portion of the center adjustment portion 110 having threads 112 for receiving the reduction nut 125. In use, the bone engaging end 106 of the threaded fragment manipulator 100 is inserted through the a receiving hole 70 in the reduction platform and then into the fracture region where it engages the targeted fractured bone piece.

The threaded fragment manipulator 100 is of a length 102 sufficient to permit engagement to a fractured bone segment with the bone engaging end 106 and to an optional drive assembly 130 (shown in FIG. 1) on the tool engaging end 108. At least a portion of the central adjustment portion 110 has external threads 112 arranged to permit engagement of the reduction nut 125 at a point above the reduction platform 50. The threads 112 should be arranged along the central adjustment portion 110 to allow a full range of reduction adjustment using the reduction nut 125. As earlier noted, the cross section 104 of the threaded fragment manipulator is generally smaller than the receiving holes 70 in the reduction platform, thus permitting angular mobility of the threaded fragment manipulator 100 during insertion and reduction.

Figure 3B:
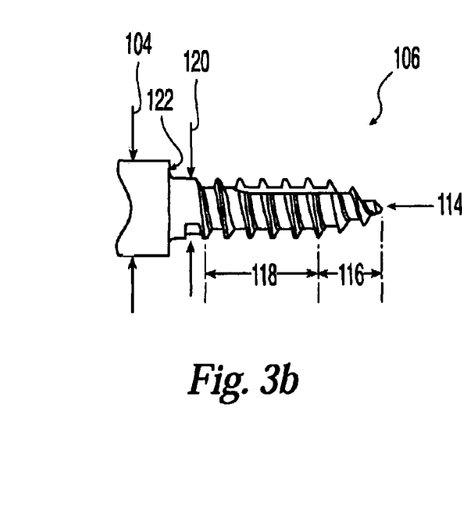
Figure 3C:
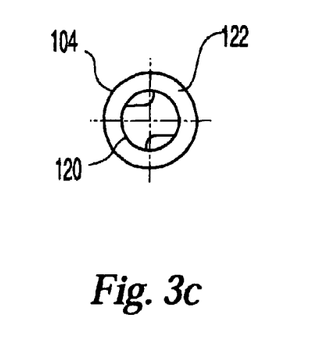

The threaded fragment manipulator bone engaging portion 106 may have a self-drilling tip 114, which permits the surgeon to engage the targeted bone fragment without the need for pre-drilling or tapping. The self-drilling tip 114 has first portion 116 and second portion 118 as depicted in FIG. 3B. The first portion 116 has threads that increase in diameter as they move away from the screw tip 114 and the second portion 118 having uniform diameter threads. The increasing diameter threads of the first portion 116 are adapted to self engage and penetrate the fractured bone piece without pre-drilling of a pilot hole. The uniform diameter threads of the second portion 118 are adapted to securely attach the fractured bone fragment once engaged. The bone engaging portion 106 may have an outer diameter 120 less than the central cross section 104 of the threaded fragment manipulator, thus providing a longitudinal stop 122, whereby unlimited insertion of the threaded fragment manipulator 100 into the bone fragment is prevented.

Figure 3D:
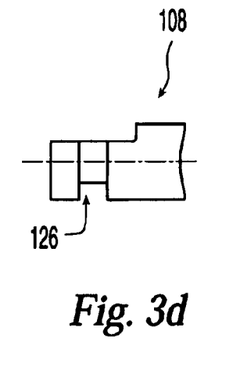
Figure 3E:
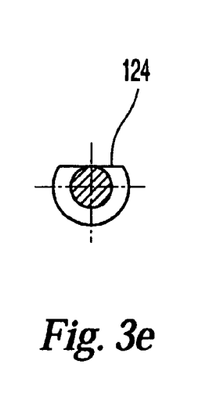
Figure 3F:
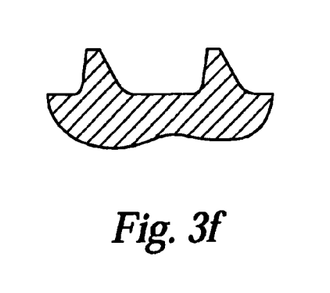

The threaded fragment manipulator tool engaging end 108 may have a coupling surface for engaging an optional drive assembly 130 (shown in FIG. 1). The drive assembly 130 may include any appropriate hand operated device, such as a screw driver, a ratchet type device, or any appropriate motorized device, such as a low rpm drill, for example, a battery powdered drill or screw driver. The coupling surface may be configured in any manner appropriate for attaching the threaded fragment manipulator 100 to the drive assembly 130. Such configurations may include straight bit connectors, hex bits, clamp, ratchet type connection, etc. In one embodiment, the coupling surface is a D-shape rod 124 having a notch 126, commonly known in the industry a mini quick coupling, as depicted in FIGS. 3D and 3E, for securing the threaded fragment manipulator 100 to the drive assembly 130, which has a correspondingly shaped engagement feature. Alternatively, the tool engaging end 108 and the drive assembly 130 may be integrally formed.

The center adjustment portion 110 of the threaded fragment manipulator 100 is preferably located between the tool engaging end 108 and the bone engaging end 106, and along at least a portion of its length, has external threads 112 configured to receive the reduction nut 125. Once the threaded fragment manipulator 100 is engaged with a bone fragment, the reduction nut 125 is threaded onto the threaded fragment manipulator 100 until the nose 127 of the reduction nut contacts the reduction platform 50 (as shown in FIG. 4). The nose 127 of the reduction nut may comprise a spherical, rounded, angled or any other appropriate shaped tip, to allow multi-angle contact with the reduction platform 50, preferably with the countersunk receiving holes 70. Having a spherical nose 127 allows the threaded fragment manipulator 100 to be installed at various angles relative to the axis 72 of the receiving holes, while still permitting the reduction nut 125 and reduction platform 50 to be in full contact. Alternatively, the nose 127 can be flat.

Continued rotation of the reduction nut 125 causes the threaded fragment manipulator 100 to be drawn up through the reduction nut 125, pulling the bone fragment toward the reduction platform 50, thereby reducing the fracture. This arrangement permits accurate control over reduction distances which is determined by the pitch of the threads. Turning of the reduction nut 125 allows reduction in small increments. The amount of reduction per rotation of the nut 125 is determined by the pitch of the threads 112, and may be adjusted to suit the particular application.

In an alternate embodiment, the threaded fragment manipulator 100 may be configured such that the bone engaging end 106 and the center adjustment portion 110 are in axial contact with one another, but after insertion of the threaded fragment manipulator 100 into the fractured bone piece, the bone engaging end 106 and the center adjustment portion 110 may become rotationally uncoupled, that is, rotation of the center adjustment portion 110 may thereafter be independent from rotation of the bone engaging end 106. This permits the surgeon to rotate the center portion 110 of the threaded fragment manipulator 100 while the bone engaging end 106 remains rotationally stationary, thus permitting the threaded fragment manipulator 100 to be drawn out, while permitting the bone engaging portion 106 to remain in threaded engagement with the fractured bone piece, thus pulling the fractured bone piece upward toward the reduction platform 50 without the use of a reduction nut 125. This rotational uncoupling may be accomplished by any means known in the field, including but not limited to a ratchet type assembly whereby the center adjustment portion 110 and the bone engaging end 106 are rotationally uncoupled in only one rotation direction. In this embodiment, the two portions remain axially fixed, and are also fixed rotationally in a forward direction so that they may rotated together to engage the fragment bone piece. The center portion 110, however, is free to rotate in the opposite direction with respect to bone engaging portion 106, so that reverse rotation of the center portion 110 does not cause the threaded fragment manipulator 100 to disengage the bone fragment. Alternatively, the center adjustment portion 112 and bone engaging end 106 may be rotationally connected by a connection means so that after the threaded fragment manipulator 100 is inserted, the connection means may be disengaged so that the bone engaging end 106 and the center adjustment portion 110 become rotationally uncoupled, for example, such connection means includes a collar, a pin, etc.

The threaded fragment manipulator 100 and reduction nut 125 can be manufactured from a variety of materials, including but not limited to titanium, titanium alloy, aluminum, stainless steel, etc.

The reduction platform 50 may be supported above the fractured region of the skull by any supporting system 150 known in the art. For example, the reduction platform 50 may be supported using standard external frames widely known in the field and may also be connected to standard head fixation assemblies, for example, Mayfield Head Holders. Alternatively, and as shown in FIG. 5, the reduction platform 50 may be supported above the fractured skull by a customized external frame 200.

Figure 5:
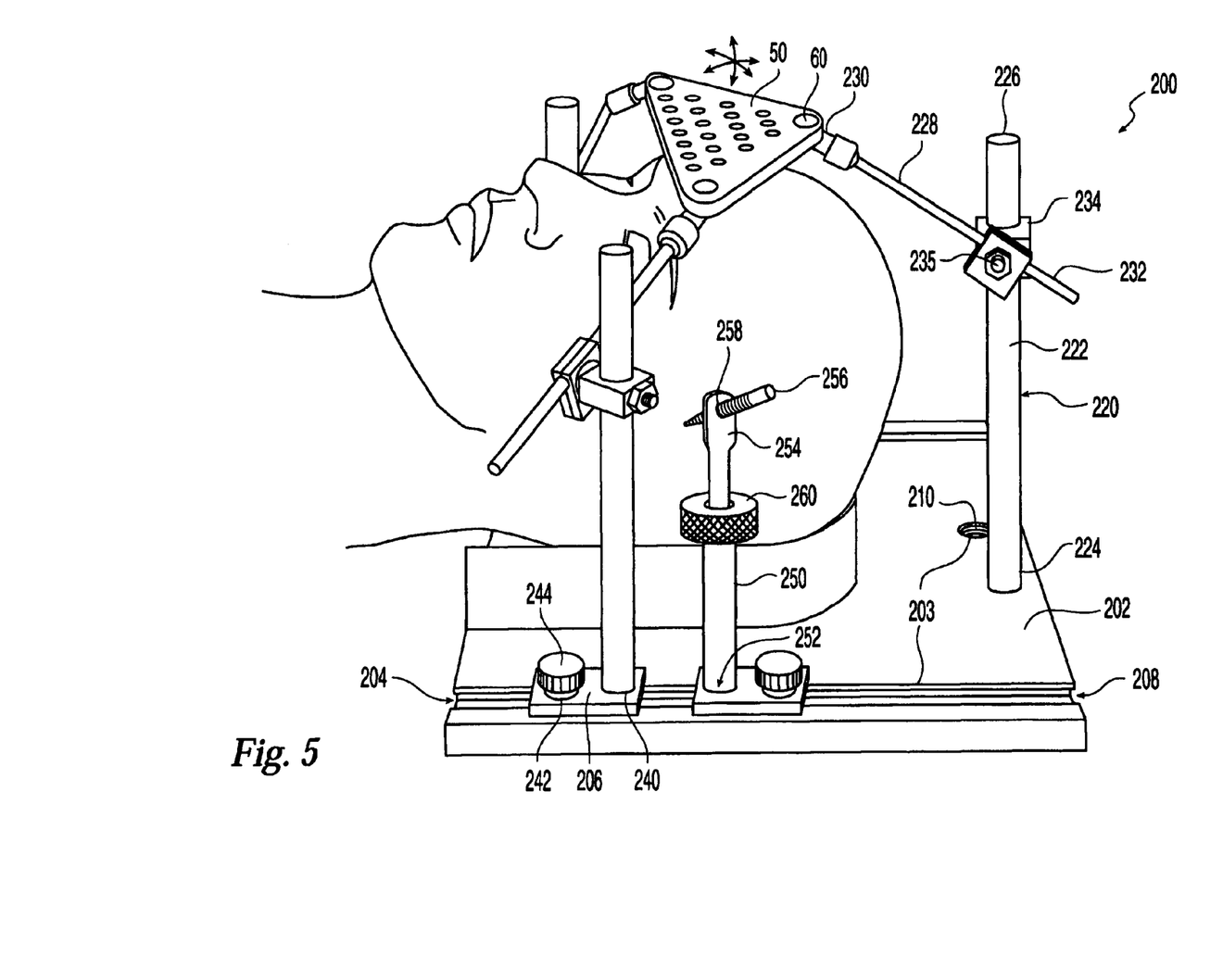
FIG. 5 is a perspective view of the Craniofacial Fracture Reduction Assembly of FIG. 1 utilizing an external frame during operation.

The external frame 200 of FIG. 5 includes a head support plate 202 and a plurality of post assemblies 220. The head support plate 202 may have different types of adjusting mechanisms 203 which allow the post assemblies 220 to be positioned in a wide variety of locations, which, in turn, facilitate the placement of the reduction platform 50 anywhere above the patient's skull.

As further illustrated in FIG. 5, the adjustment mechanism 203 may include one or more sliding track adjustment assemblies 204, which may include sliding plates 206 having at least a portion of which is designed to be inserted into a track 208 in the head support assembly 202. Preferably, the track 208 and the sliding plates 206 have a corresponding shape. Furthermore, the track 208 preferably is straight providing linear movement. Movement of the sliding plate 206 within the track 208 allows movement of the post assemblies 220 in relation to the head support 202. Each sliding plate 206 generally includes a plurality of threaded holes; one hole 240 for receiving a post assembly 220, the other hole 242 for receiving a screw 244 for locking the position of the sliding plate 206 and post assemblies 220 along the sliding track assembly 204.

In an alternate embodiment, at least one of the sliding plates 206 may be configured to permit rotation of the post assembly 220 within the track 208 to permit the surgeon a wider variety of placement options. For example, the sliding plate 206 may be held within the track 208 by a cylindrical foot portion, rather than the rectangular foot portion illustrated. Use of a cylindrical foot portion may allow the surgeon to selectively rotate the foot within the track 208 about the vertical axis of the screw 244, thus enabling the sliding plate 206 and its attached post assembly 220 to pivot about the screw 244. Thus the post assembly 220 may be placed nearer or farther from the patient's head, as necessary.

Alternatively the adjustment mechanism 203 may comprise a plurality of threaded hole adjustment assemblies 210 placed at various locations on the head support plate 202 to allow threadable attachment to the post assemblies 220.

As depicted in FIG. 5, the external frame 200 preferably includes two sliding track adjustment assemblies 204 located along each side the patient's head and two threaded hole adjustment assemblies 210 located above the patient's head. In use, the external frame 200 may comprise only sliding track adjustment assemblies 204 or only threaded hole adjustment assemblies 210. Furthermore, any number and combination of sliding track adjustment assemblies 204 and threaded hole adjustment assemblies 210 may be used in any number of locations.

Each post assembly 220 may comprise a vertical connecting post 222, a connecting rod 228, and an adjustable clamp 234. The vertical connecting post 222 has a first end 224 and second end 226, the first end 224 adapted for fixation to the head support table 202 and the second end 226 adapted for receipt of the adjustment clamp 234. Similarly, each connecting rod 228 may include first end 230 and second end 232. The first end 230 may be adapted for connection to one or more fixation elements 60 in the reduction platform 50. This connection can be accomplished by any known means in the art including, but not limited to, friction fit, brazing, threading, screw and nut connection, etc. In one embodiment, the first end 230 is connected to the reduction platform 50 by a universal joint and the second end 232 is connected to the adjustment clamp 234.

The adjustment clamp 234 permits three dimensional adjustment allowing the surgeon to precisely locate the reduction platform 50 over the fracture region. The adjustment clamp 234 may be slidable along the vertical connecting posts 222 and may be locked to the vertical connecting post 222 at any location along the vertical connecting post 222. Preferably, the adjustment clamp 234 is locked to the vertical connecting post 222 by a bolt (not shown). Furthermore, the adjustment clamp 234 may permit the connecting rod 228 to be moved in and out of the adjustment clamp 234. Preferably, the connecting rod 228 is locked to the adjustment clamp 234 by a bolt (not shown). More preferably, the bolt for locking the adjustment clamp 234 to the vertical connecting post 222 and the bolt for locking the connecting rod 228 to the adjustment clamp 234, is the same bolt 235, thus permitting a surgeon to lock the reduction platform 50 in any location by the turning of a single bolt 235.

As further depicted in FIG. 5, the external frame 200 may comprise of a number of head stabilizing assemblies 250, each having a support plate engaging portion 252 and a fixation pin engaging portion 254. The support plate engaging portion 252 may be threaded to engage a sliding plate 206, as described above in connection with the vertical connecting posts 222. Alternatively, the threaded portion may thread directly into one of the threaded holes 210 of the head support plate 202. The fixation pin engaging portion 254 may have a threaded bore 258 configured to receive the threaded body portion of at least one scalp fixation pin 256. Upon assembly, the scalp fixation pins 256, in combination with the head stabilizing assemblies 250, prevent patient head movement during the reduction process. The head stabilizing assemblies 250 may further include a height adjusting mechanism 260, thus permitting a surgeon to vary the height of the scalp fixation pins 256. As depicted, the height adjusting mechanism 260 is a knob, which when loosened permits the fixation pin engaging portion 254 to slide within the support plate engaging portion 252 however, when tightened the height adjusting mechanism prevents relative movement between the fixation pin engaging portion 254 and the support plate engaging portion 252. Although depicted as a knob, it should be noted that any means known in the art may be used to perform the stated function.

Alternatively as best illustrated in FIG. 8, the head stabilizing assemblies 250 may comprise an outer support plate engaging portion 550 and an inner fixation pin engaging portion 552. The inner portion 552 may have a first end and a second end, wherein the first end may be sized and configured to be telescopically received in the outer portion 550 thus permitting the surgeon to vary the overall height of the head stabilizing assemblies 250. The head stabilizing assemblies 250 may further include a set screw 556 for fixedly securing the position of the inner portion 552 with respect to the outer portion 550 once the skull fixation pins are located in a desired position. The second end of the inner portion 552 may have a threaded bore 557 for receiving a threaded screw 558 which is fixedly connected to an extension member 560, which may include a plurality of bores for receiving skull fixation pins therethrough.

In an alternate embodiment, the reduction platform 50 may be used without the adjustment mechanism of FIG. 5. In this embodiment, the reduction platform 50 is supported over the fractured skull using support legs 275 as shown in FIG. 4. The support legs 275 may each have a fixation end 278 and a patient end 280. The fixation end 278 may be adapted for connection to the fixation elements 60 of the reduction platform 50. This engagement can be accomplished by any known means in the art including, but not limited to friction fit, threading, brazing, welding, universal joint, etc. The patient end 280 of the support legs 275 may have any suitable surface for contacting the patient's face. Alternatively, the patient end 280 may comprise suction cups, which are attached to the patient's face.

Figure 6:
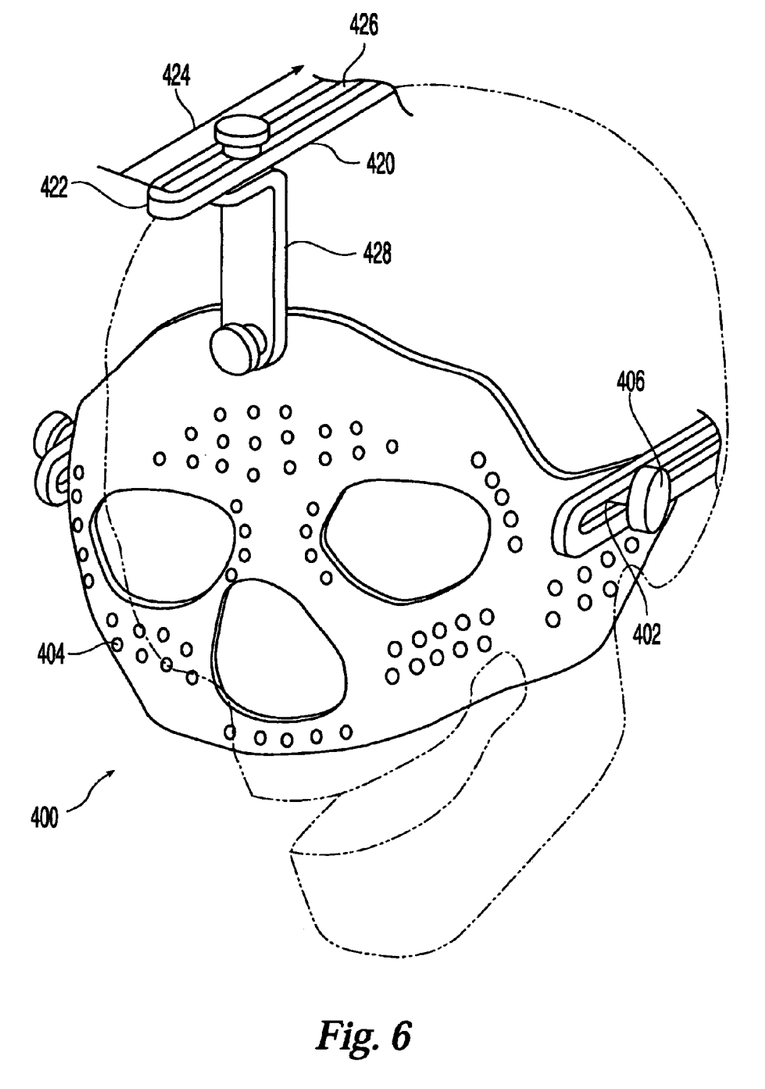
FIG. 6 is a perspective view of an alternate embodiment of the reduction platform.

An alternative embodiment of the invention is shown in FIG. 6, in which the reduction platform comprises a mask-like structure 400. As with the previous embodiments, mask 400 has top and bottom surfaces and at least one receiving hole 404 disposed therebetween. Fixation elements 402 may be provided at top and side portions of the mask 400, to allow connection of the mask 400 to a support assembly 150, shown here as a set of sliding frame elements 420 which are described below in more detail. The mask reduction frame 400 may incorporate eye and nose cut outs, although such cut outs are not considered necessary.

As with previously-described embodiments, the mask type reduction platform 400 may be supported above the fracture region by any means known in the art including any one or combination of the systems described above. As shown in FIG. 6, the external frame may comprise a plurality of side and top sliding frame elements 420, the sliding frame elements 420 each having a first end (not shown), a second end 422 and a center portion 424 disposed between the first and second end 422. The first end may be adapted for fixation to the head support table (not shown) by any means known in the art, including but not limited to threadedly engaging a sliding plate or threaded hole, as previously described. The center portion 424 may have a longitudinal slot 426 for slidably adjusting the mask reduction platform 400 along each sliding frame element 420. The longitudinal slot 426 may be sized to receive a screw fixation pin 406 for locking the position of the mask relative to the sliding frame element 420. One or more extension pieces 428 may be used to connect the fixation elements 402 to the sliding frame element 420.

It is noted that the number and arrangement of receiving holes 404 and optional fixation elements 402 may vary according to the size and coverage of the particular mask reduction platform 400 used, and according to the arrangement of the corresponding support assembly.

Figure 7:
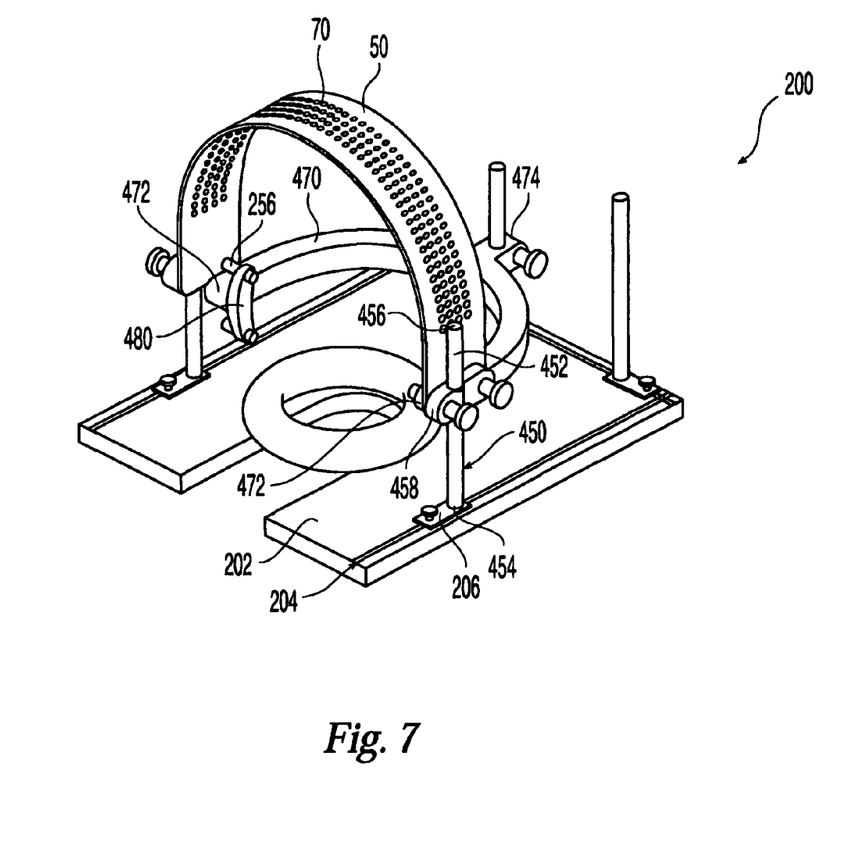
FIG. 7 is a perspective view of a different alternate embodiment of the reduction platform and external frame.

An alternate embodiment of the reduction platform 50 and external frame 200 is depicted in FIG. 7. In this embodiment the external frame 200 comprises a head support plate 202 and a plurality of post assemblies 450. The head support plate 202 may have multiple adjusting mechanisms 203 which allow the post assemblies 450 to be positioned in a wide variety of locations, which, in turn facilitate the placement of the reduction platform 50 anywhere over the patient's skull. As depicted, the adjustment mechanism 203 may comprise a plurality of sliding track adjustment assemblies 204 and sliding plates 206, as described above. This embodiment includes three sliding track assemblies 204, one located on each side of the patient's head and one located above the patient's head.

The two side post assemblies 450 each comprise a vertical connecting post 452 and a post to platform clamp 458. The vertical connecting post 452 has first 454 and second ends 456, the first end 454 adapted for fixation to the head support plate 202, as previously described, and the second end 456 adapted for slidably receiving the post to platform clamp 458. The post to platform clamp 458 is adapted to engage the reduction platform 50. This connection can be accomplished by any means known in the art including, but not limited to, threading (as depicted), friction fit, brazing, screw and nut connection, etc. Using a slidable post to platform clamp 458 permits the surgeon to adjust the height of the reduction platform 50 to suit the individual patient.

The reduction platform 50, as depicted, is a rectangular plate having an arched profile, a plurality of receiving holes 70, and at least one fixation element 60, the receiving holes 70 and fixation elements 60 having the attributes as described above in relation to previous embodiments. The arched reduction platform 50 extends between the side post assemblies 450, with the top of the arch platform positioned so as to be located over the fractured bone region when the patient's head is placed on the head support plate 202.

The external frame 200 may further comprise an arched lateral brace 470 having first and second ends 472, located on opposite sides of the patient's head, and an intermediate center portion 474, located adjacent the crown of the head. The first and second ends 472 may have a threaded connection for fixation to the post to platform clamp 458, however, any suitable connection known in the art may be used, including but not limited to, friction fit, welding, brazing, screw and nut connection, etc. The first and second ends 472 may further comprise a hanger extension piece 480 including at least one scalp fixation pin 256 for securing the patient's head during the reduction procedure, thus eliminating the need for head stabilizing assemblies 250 as previously described. The intermediate center portion 474 may further have an attachment for slidably engaging a post assembly 450.

Although the embodiment has been described as depicted in FIG. 7, it should be noted that alternate embodiments are envisioned. For example, the adjustment mechanism 203 may include a plurality of threaded hole adjustment assemblies 210 placed at various locations on the head support plate 202. Furthermore, in use, the external frame 200 may include any number of sliding track assemblies 204 or a combination of sliding track adjustment assemblies 204 and threaded hole adjustment assemblies 210. Also, although described as a rectangular reduction platform, it should be noted that any shape can be used as described above. Furthermore, the reduction platform 50 may contain any number of receiving holes 70 and fixation elements 60, arranged in any number of configurations depending on the size and shape of the reduction platform 50 used. Finally, the external frame 200 may also contain head stabilizing assemblies 250, as described above.

Alternatively, as shown in FIGS. 8 and 9, the reduction platform 50 may be a cylindrical bar 500 containing any number of receiving holes 70 for receiving the threaded fragment manipulator 100 (as previously described) and the external frame 200 may comprise a head support plate 202 incorporating a plurality of support members 510 having an arched profile sized and configured to extend from one side of the head support plate 202 to another side of the head support plate 202, with the top of the arch support members 510 being configured to extend over the patient's skull.

As previously described, the head support plate 202 may include different types of adjusting mechanisms 203 which allow the arched support members 510 to be positioned in a wide variety of locations, which, in turn, facilitate the placement of the reduction platform 500 in a desired location above the patient's skull. The adjustment mechanism 203 may include, inter alia, either alone or in combination, one or more sliding track adjustment assemblies 204 and/or a plurality of threaded hole adjustment assemblies 210 as previously described. The head support plate 202 may also include at least one head stabilizing assembly 250 as previously described. As shown, the arched support members 510 may be connected to the head support plate 202 by a pair of engagement clamps 530 which may be slidably received within the sliding track adjustment assemblies 204 (FIG. 7). The sliding track adjustment assemblies 204 may also include a plurality of holes 532 sized and configured to receive a portion of the arched support members 510. As shown, the portion of the support members 510 received within the holes 532 is substantially straight so that the surgeon can move the support members 510 in a vertical direction, in and out of the holes 532, thereby adjusting the overall height of the arched support members 510 with respect to the head support plate 202. This also permits the surgeon to adjust the height of one support member 510 with respect to the other, thus permitting the surgeon to angularly adjust the reduction platform 500 attached thereto. Moreover, the support members 510 may include a thumb wheel 570 (to be described in more detail later) between the straight portion of the support members 510 and the engaging holes 532, thus, providing a surgeon with the ability to incrementally and precisely adjust the vertical height of the support members 510. The engagement clamps 530 may also each include a set screw 534 to fixedly secure the placement of the arched support members 510, as commonly known in the art, once the platform 500 is located in a desired location.

As shown, the cylindrical reduction platform 500 is sized and configured to engage the arched support members 510 to be located over the targeted bone region. The cylindrical reduction platform 500 may engage the arched support members 510 by any appropriate means known in the art. In the illustrated embodiment, the cylindrical reduction platform 500 is slidably engaged to the arched support members 510 so that the surgeon can slidably move the reduction platform 500 along the arched members 510. As best shown in FIG. 9, the reduction platform 500 may include a connection clamp 520, the clamp 520 having a first bore 522 sized and configured to the receive the reduction platform 500 and a second bore 524 sized and configured to receive the arched support members 510. The connection clamp 520 may also include a set screw 526 to fixedly secure the location of the reduction platform 500 once the platform 500 is located in a desired location. Moreover, as previously discussed, the cylindrical bar 500 may include at least a portion with external threads (not shown) for engagement with a thumb wheel 570. That is, as best illustrated in FIG. 9, the cylindrical bar 500 may also include a thumb wheel 570 with an internally threaded sleeve 572 protruding therefrom. The sleeve 572 is sized and configured to fit between the cylindrical bar 500 and the first bore 522 of the connection clamp 520. Rotation of the thumb wheel 570 may cause the bar 500 to translate with respect to the thumb wheel 570, thus permitting the surgeon to incrementally and precisely adjust the position of the cylindrical bar 500 with respect to the support member 510 which is contacted by the thumb wheel 500. Preferably, the thumb wheel 570 is arranged to provide superior-inferior adjustment of the cylindrical bar 500 with respect to a patient's skull.

The present invention may further utilize an endoscope 300, which is a long slender medical instrument for examining areas interior to the body. An endoscope 300 may permit the surgeon to view the interior of the fracture region during insertion of the threaded fragment manipulator 100 to ensure accurate placement and proper engagement of the manipulator 100 with the fractured bone pieces. The endoscope 300 may be inserted through a small incision above the patient's hairline, thus minimizing scarring and healing time. As depicted in FIG. 1, an endoscope 300 is inserted near the forehead. The endoscope 300, however may be located in any area depending on the location of the fractured bone. Furthermore, a plurality of endoscopes 300 may be simultaneously utilized, if so desired.

A method of using a Craniofacial Fracture Reduction Assembly 10 to reduce and realign fractured bone pieces is also provided. Generally the method comprises locating fractured bone pieces in need of realignment. This may be done by visualization or with the use of an endoscope 300 or similar device. Once located, surgical elevators or spatulas may be used to prepare the fracture site and to remove any soft tissue from the targeted bone fragments. Next the reduction platform 50 may be positioned over the patient's face and secured into position. A threaded fragment manipulator 100 is then inserted through the reduction platform 50 and the bone engaging portion 106 is engaged with a bone fragment. A reduction nut 125 is then threaded onto the threaded fragment manipulator center adjusting portion 110 until the reduction nut 125 contacts the reduction platform 50. Thereafter, rotation of the reduction nut 125 causes the threaded fragment manipulator 100 to be drawn up through the reduction nut 125, reducing the bone piece attached to the bone engaging portion 106.

If necessary, a surgeon may use a plurality of threaded fragment manipulators 100. Utilizing multiple threaded fragment manipulators 100 permits the surgeon to use gradual incremental reduction on multiple fractured bone pieces or on a single larger fractured bone piece.

Note, while it is disclosed that the reduction platform 50 is positioned prior to installation of the threaded fragment manipulator 100, this specific sequence is not necessary. For example, the threaded fragment manipulator 100 may first be engaged with a bone fragment and then the reduction platform 50 may be installed over the threaded fragment manipulator 100, followed by installation of the reduction nut 125. Alternatively, the reduction platform 50 may be positioned first, then the threaded fragment manipulator 100 installed. Thereafter the reduction platform 50 may be removed and/or relocated, if necessary, followed by refastening of the threaded fragment manipulator 100 to the reduction platform 50. It is noted that the order of the above steps may be further modified by the surgeon to achieve the most efficient and appropriate reduction procedure for a particular patient using the disclosed device.

The Craniofacial Fracture Reduction Assembly 10 of the present invention may also be provided as a kit having various components (e.g., platforms, manipulators, reduction nuts, etc.) which allow the surgeon to select from a variety of pieces to optimize the Craniofacial Fracture Reduction Assembly 10 for individual patient. For example, a kit may include several different threaded fragment manipulators 100 having varying cross sections 104 and lengths 102. Additionally, the kit may contain similarly sized threaded fragment manipulators 100 having the same or different sized bone engaging tips 106, or the same or different center adjusting thread pitches 112, the different thread pitches varying the amount of reduction per rotation of nut 125. Furthermore, the Craniofacial Fracture Reduction Assembly 10 may include a variety of different support assemblies 150, for example, it may include a custom external frame 200, or it may include connections for attaching the reduction platform 50 to an existing external frame already in the surgeon's possession. Alternatively, the assembly may include support legs 275.

The present invention has been described in connection with the preferred embodiments. These embodiments, however, are merely for example and the invention is not restricted thereto. It will be understood by those skilled in the art that other variations and modifications can easily be made within the scope of the invention as defined by the appended claims, thus it is only intended that the present invention be limited by the following claims.

What is claimed is:

1. A method of performing craniofacial reduction on a head of a patient comprising:
   positioning adjacent the head of the patient a supporting structure for adjustably securing a reduction platform, the reduction platform having means for fixation to the supporting structure;
   adjustably securing the reduction platform to the supporting structure;
   locating a fractured bone portion to be reduced that is located adjacent a second bone portion;
   positioning the reduction platform above the surface of the head of the patient and over the fractured bone portion, the reduction platform having a plurality of circular bores configured to have a diameter to receive a fragment manipulator and a top surface;
   inserting a fragment manipulator through one of the bores of the reduction platform wherein the fragment manipulator has a threaded, bone-engaging end portion;
   engaging the fractured bone portion with the bone-engaging end of the fragment manipulator;
   threading a nut onto the fragment manipulator until the nut contacts the reduction platform; and
   rotating the nut so that the fragment manipulator is drawn up through the nut to pull the located, fractured bone portion attached to the fragment manipulator toward the reduction platform and thus changing the relative position of the fracture bone portion and the adjacent, second bone portion.

2. The method of claim 1, wherein the fragment manipulator includes a threaded central portion located proximally from the bone-engaging end portion, the manipulator further having a portion which is sized to fit within at least one reduction platform bore.

3. The method of claim 2, further comprising threadably engaging the nut with the threaded central portion of the manipulator.

4. The method of claim 3, wherein the nut further includes a spherical nose for engaging the top surface of the reduction platform, the nose being configured to facilitate angular adjustment of the fragment manipulator with respect to the reduction platform.

5. The method of claim 2, wherein the bone-engaging end portion of the fragment manipulator has a self-drilling tip.

6. The method of claim 1, wherein the fragment manipulator further includes a tool engaging portion.

7. The method of claim 1, wherein the reduction platform has a plate-like configuration.

8. The method of claim 1, wherein the reduction platform is a mask-like configuration.

9. The method of claim 1, wherein the reduction platform is a rectangular plate having an arched profile.

10. The method of claim 9, wherein the supporting structure further includes a head support plate and a plurality of support members having an arched profile sized and configured to extend from a first side of the head support plate to a second side of the head support plate, with the top of the arch support members being configured to extend over the patient's head.

11. The method of claim 1, wherein the reduction platform is a cylindrical bar and the supporting structure comprises a plurality of arched support members.

12. The method of claim 11, wherein the cylindrical bar includes a connection clamp having a first bore and a second bore, the first bore being sized and configured to the receive the cylindrical bar and the second bore being sized and configured to receive at least one of the arched support members.

13. The method of claim 12, further comprising a thumb wheel having an internally threaded sleeve for engaging an externally threaded portion on the cylindrical bar wherein the sleeve of the thumb wheel is sized and configured to be installed between the first bore and the cylindrical bar for incrementally adjusting the position of the bar with respect to the supporting structure.

14. The method of claim 12, wherein the supporting structure comprises an external frame including a head support plate and a plurality of post assemblies.

15. The method of claim 1, wherein the supporting structure comprises a plurality of arched support members.

16. The method of claim 1, wherein the reduction platform includes a plurality of support legs for positioning the reduction platform above the targeted bone region.

* * * * *